United States Patent
Wartenberg et al.

(10) Patent No.: US 6,723,848 B2
(45) Date of Patent: Apr. 20, 2004

(54) METHOD FOR PRODUCING BENZO ANNELATED HETEROCYCLES

(75) Inventors: Frank-Hardi Wartenberg, Darmstadt (DE); Thomas Koppe, Schaffhausen (CH); Walter Wetzel, Darmstadt (DE); Markus Wydra, Roedermark (DE); Achim Benz, Darmstadt (DE)

(73) Assignee: Merck Patent Gesellschaft mit Beschränkter Haftung, Darmstadt (DE)

( * ) Notice: Subject to any disclaimer, the term of this patent is extended or adjusted under 35 U.S.C. 154(b) by 0 days.

(21) Appl. No.: 10/257,139

(22) PCT Filed: Mar. 9, 2001

(86) PCT No.: PCT/EP01/02672
§ 371 (c)(1),
(2), (4) Date: Oct. 9, 2002

(87) PCT Pub. No.: WO01/77099
PCT Pub. Date: Oct. 18, 2001

(65) Prior Publication Data
US 2003/0078422 A1 Apr. 24, 2003

(30) Foreign Application Priority Data
Apr. 11, 2000 (DE) .......................... 100 17 947

(51) Int. Cl.[7] .................. C07D 401/00; C07D 209/02; C07D 333/66; C07D 307/78
(52) U.S. Cl. .................. 544/333; 548/483; 549/55; 549/57; 549/467
(58) Field of Search .................. 544/333; 548/483; 549/55, 57, 467

(56) References Cited

U.S. PATENT DOCUMENTS

| 4,888,432 A | 12/1989 | Hamprecht |
| 5,869,486 A | * 2/1999 | Lee et al. .................. 514/248 |

FOREIGN PATENT DOCUMENTS

| WO | WO 94/28902 | * 12/1994 |
| WO | WO 99/55708 A1 | 4/1999 |
| WO | WO 00/78767 A1 | * 12/2000 |

* cited by examiner

*Primary Examiner*—Deborah C Lambkin
(74) *Attorney, Agent, or Firm*—Millen, White, Zelano & Branigan, P.C.

(57) ABSTRACT

Process for the preparation of benzo-fused heterocycles of general formula I:

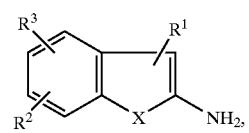

in which X, $R^1$, $R^2$, $R^3$, $R^4$, $R^5$ and n are as defined in claim 1, by reacting tetrahydrobenzo-fused heterocycles of formula II:

in which X, $R^1$, $R^2$, $R^3$, $R^4$, $R^5$, n and Ac are as defined in claim 1, with a catalytic amount of a noble metal catalyst in the presence of a hydrogen acceptor and then deacylating the acylated amino group by the addition of an amine.

16 Claims, No Drawings

METHOD FOR PRODUCING BENZO ANNELATED HETEROCYCLES

The invention relates to a process for the preparation of benzo-fused heterocycles of general formula I:

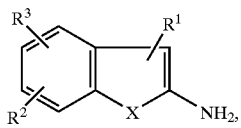

in which
X is S, O or NH,
$R^1$ is CN, $NO_2$, Ac, COAr, COOAr, COOH, COOA or $CONR^4R^5$,
$R^2$ and $R^3$ independently of one another are each H, A, $NO_2$, CN, OH, OA or Ac,
$R^4$ and $R^5$ independently of one another are each H, A, Ar or Ac, or
$R^4$ and $R^5$ together are —$(CH_2)$—$(CH_2)_n$—$(CH_2)$—,
A is alkyl having 1–6 C atoms,
Ac is acyl having 1–6 C atoms,
Ar is unsubstituted phenyl or phenyl substituted by A, $NO_2$, CN, OH or OA, and
n is 2, 3 or 4,
by reacting tetrahydrobenzo-fused heterocycles of formula II:

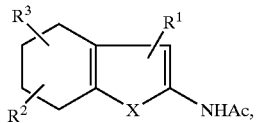

in which
X is S, O or NH,
$R^1$ is CN, $NO_2$, Ac, COAr, COOAr, COOH, COOA or $CONR^4R^5$,
$R^2$ and $R^3$ independently of one another are each H, A, $NO_2$, CN, OH, OA or Ac,
$R^4$ and $R^5$ independently of one another are each H, A, Ar or Ac, or
$R^4$ and $R^5$ together are —$(CH_2)$—$(CH_2)_n$—$(CH_2)$—,
A is alkyl having 1–6 C atoms,
Ac is acyl having 1–6 C atoms,
Ar is unsubstituted phenyl or phenyl substituted by A, $NO_2$, CN, OH or OA, and
n is 2, 3 or 4,
with a catalytic amount of a noble metal catalyst in the presence of a hydrogen acceptor and then deacylating the acylated amino group by the addition of an amine.

Benzo-fused heterocycles of formula I are important intermediates in industrial organic synthesis, e.g. in the manufacture of fine chemicals, dyestuffs and plant protection agents. They are also important intermediates in the manufacture of drugs. Benzo-fused heterocycles of formula I in which X is S are particularly important in the manufacture of PDE-V inhibitors, which are known from WO 99/55708 and WO 00/78767. In particular, ethyl 2-aminobenzo[b]thiophene-3-carboxylate is an intermediate in the synthesis of 4-[4-(3-chloro-4-methoxybenzylamino) benzo[4,5]thieno[2,3-d]pyrimidin-2-yl] cyclohexanecarboxylic acid, which is known from WO 99/55708, or 4-[4-(3-chloro-4-hydroxybenzylamino)benzo [4,5]thieno[2,3-d]pyrimidin-2-yl]cyclohexanecarboxylic acid, which is known from WO 00/78767.

According to the classical synthesis, tetrahydrobenzo-fused compounds are aromatized by reaction with elemental sulfur at high temperatures (literature: Gewald et al., Chem. Ber. 1968, 101, 1933). The disadvantages of this process are the high energy costs due to high reaction temperatures, the release of hydrogen sulfide, which is an odour nuisance, and the problems which arise in the purification, because elemental sulfur dissolves only in $CS_2$, which is very highly flammable.

One particular example from the state of the art is the reaction of the compound 2-acetylamino-3-methoxycarbonyl-4,5-tetramethylenethiophene with 2 equivalents of sulfur and dimethyl phthalate at temperatures of between 200 and 220° C. according to G. Hallas et al., Dyes Pigm. 1997, 35, 219–237. 2-Acetylamino-3-methoxycarbonylbenzo[b]thiophene is isolated and then, in a second step, deacetylated in ethanol by reaction with aqueous potassium hydroxide solution.

Another known possibility for aromatizing a tetrahydrobenzo-fused compound is to react it with an equimolar amount of a hydrogenation catalyst. One particular example, namely the dehydrogenation of methyl 2-acetylaminotetrahydrobenzothiophene-3-carboxylate with an approximately equimolar amount of palladium on carbon (10% Pd/C) in chloroform as solvent, is described in Eiden et al., Arch. Pharm. 1984, 317, 675–680.

For ecological reasons, reactions with elemental sulfur are impracticable on the industrial scale.

In the second variant, the amount of hydrogenation catalyst used should be kept as small as possible for economic reasons. Also, the benzo-fused heterocycles formed in the dehydrogenation are often only sparingly soluble in the solvents used and precipitate out when the heterogeneous reaction mixture cools. This makes separation of the noble metal catalyst more difficult and considerable amounts of solvent are required to extract the product from the noble metal catalyst.

The object of the invention was therefore to develop a process for the preparation of benzo-fused heterocycles of formula I which has advantages over the known processes of the state of the art.

Surprisingly, it was found that tetrahydrobenzo-fused compounds of formula II can be aromatized with a catalytic amount of a hydrogenation catalyst in the presence of a hydrogen acceptor. Immediate deacylation of the amino group in the 2-position of the heterocycle by the addition of an amine provides the benzo-fused compounds of formula I as readily soluble products, enabling the noble metal catalyst to be separated off by simple filtration. The process according to the invention is a one-pot process, i.e. the aromatization and deacylation take place in succession without isolation of the intermediate, which in this case is the benzo-fused heterocycle with its amino group acylated.

The meanings of all the radicals which occur several times, e.g. A or Ac, are independent of one another.

The radical A is alkyl and has 1 to 6, preferably 1, 2, 3 or 4 and particularly preferably 1 or 2 C atoms. Alkyl is therefore especially e.g. methyl, also ethyl, n-propyl, isopropyl, n-butyl, sec-butyl or tert-butyl, or also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl or 1,1,2- or 1,2,2-trimethylpropyl. A is particularly preferably methyl or ethyl.

Ac is acyl and preferably has 1–6 C atoms. Ac is e.g. formyl, acetyl, propionyl, butyryl, pentanoyl or hexanoyl, or also trifluoroacetyl. Ac is particularly preferably acetyl.

Ar is unsubstituted phenyl or phenyl substituted by A, $NO_2$, CN, OH or OA.

Ar is therefore preferably phenyl, o-, m- or p-methylphenyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-methoxyphenyl, o-, m- or p-ethoxyphenyl, o-, m- or p-nitrophenyl or o-, m- or p-cyanophenyl. Ar is particularly preferably unsubstituted phenyl.

COAr is aroyl, Ar being as defined above. COAr is particularly preferably benzoyl.

COOAr is aryloxycarbonyl, Ar being as defined above. COOAr is particularly preferably phenoxycarbonyl.

X is S, O or NH, S being particularly preferred.

$R^1$ is CN, $NO_2$, Ac, COAr, COOAr, COOH, COOA or $CONR^4R^5$, A, Ac and Ar being as defined above and $R^4$ and $R^5$ being as defined below. $R^1$ is particularly preferably CN or COOA and very particularly preferably COOA.

$R^2$ and $R^3$ independently of one another are each H, A, $NO_2$, CN, OH, OA or Ac, A and Ac being as defined above. $R^2$ and $R^3$ are particularly preferably H.

$R^4$ and $R^5$ independently of one another are each H, A, Ar or Ac, A, Ar and Ac being as defined above. $R^4$ and $R^5$ are particularly preferably H.

$R^4$ and $R^5$ together are also —$(CH_2)$—$(CH_2)_n$—$(CH_2)$—, it being possible for n to be 2, 3 or 4. $R^4$ and $R^5$ together are particularly preferably —$(CH_2)$—$(CH_2)_2$—$(CH_2)$— or —$(CH_2)$—$(CH_2)_3$—$(CH_2)$— and very particularly preferably —$(CH_2)$—$(CH_2)_3$—$(CH_2)$—.

The hydrogenation catalysts (or, synonymously, noble metal catalysts) used can be suitably supported noble metals such as palladium, platinum or rhodium, suitable supports being carbon, activated carbon, aluminium oxide, barium carbonate, barium sulfate, calcium carbonate or strontium carbonate. The proportion of noble metal in the noble metal catalyst is between 1 and 20%, preferably between 5 and 10% and particularly preferably 5%.

Palladium on activated carbon, carbon, aluminium oxide, barium carbonate, barium sulfate, calcium carbonate or strontium carbonate, platinum on activated carbon, carbon or aluminium oxide, or rhodium on carbon or aluminium oxide, can be used in particular for the process according to the invention. It is particularly preferred to use palladium on activated carbon (5% Pd).

Another possibility is to use noble metal salts which can be reduced in situ by a reducing agent and produce in situ a finely divided palladium(0) species. Examples of suitable noble metal salts are palladium acetate, palladium bromide or palladium chloride and examples of suitable reducing agents are hydrogen, hydrazine, sodium borohydride or formates.

The invention further relates to a process for the preparation of benzo-fused heterocycles of general formula I according to claim 1 or 2, characterized in that a noble metal catalyst, selected from the group comprising palladium on activated carbon, carbon, aluminium oxide, barium carbonate, barium sulfate, calcium carbonate or strontium carbonate, platinum on activated carbon, carbon or aluminium oxide, and rhodium on carbon or aluminium oxide, is used.

Inexpensive organic hydrogen acceptors, such as the ones known to those skilled in the art, are particularly suitable for the process according to the invention, examples of inexpensive organic hydrogen acceptors being styrene, α-methylstyrene, stilbene, tolans, cinnamic acid esters or cyclohexene. It is particularly preferred to use α-methylstyrene. Other hydrogen acceptors suitable for the process according to the invention are oxygen or oxygen/gas mixtures, gas being understood as meaning nitrogen or noble gases such as helium, neon, argon or xenon. The proportion of oxygen in the oxygen/gas mixture is between 1 and 99%, preferably between 10 and 50% and particularly preferably 15 to 25%. The oxygen/gas mixture is particularly preferably air.

The organic hydrogen acceptor may undergo polymerization reactions during the aromatization. The formation of these by-products, i.e. polymers, can be reduced by adding the hydrogen acceptor in small amounts, successively (semicontinuously) or continuously, during the reaction.

The invention further relates to a process for the preparation of benzo-fused heterocycles of general formula I according to one or more of claims 1 to 3, characterized in that a hydrogen acceptor selected from the group comprising styrene, α-methylstyrene, stilbene, tolans, cinnamic acid esters, for example methyl or ethyl cinnamate, cyclohexene, oxygen and oxygen/gas mixtures is used.

The dehydrogenation—and hence aromatization—using a catalytic amount of a hydrogenation catalyst should advantageously be carried out under an inert gas atmosphere in order to avoid explosions, which is why it is advantageous to use organic hydrogen acceptors selected from the group comprising styrene, α-methylstyrene, stilbene, tolans, cinnamic acid esters and cyclohexene.

To deacylate the acylated amino group of the compounds of general formula II and of the benzo-fused intermediate after aromatization, a primary or secondary amine boiling at between 50 and 200° C., preferably at between 50 and 150° C., is added to the reaction mixture. It is particularly preferred to use pyrrolidine, piperidine, piperazine, morpholine or dioctylamine and very particularly preferred to use pyrrolidine.

The invention relates to a process as described above, characterized in that a primary or secondary amine boiling at between 50 and 200° C. is selected for the deacylation.

The aromatization and deacylation preferably take place in an inert high-boiling solvent, preferred inert high-boiling solvents being benzene, toluene, xylene, mesitylene, diphenyl ether or sulfolane. Xylene is preferably used as an isomeric mixture. The isomers o-, m- or p-xylene are also suitable. It is particularly preferred to use xylene.

The invention relates to the process described above, characterized in that the reactions are carried out in an inert high-boiling solvent.

The dehydrogenation and deacylation preferably take place at temperatures of between 50° and 250° C., the temperature range for the dehydrogenation being preferably between 100° and 250° C. and particularly preferably between 140° and 200° C., and the temperature range for the deacylation being preferably between 50° and 200° C. and particularly preferably between 80° and 150° C.

The invention relates to the process described above, characterized in that the reactions are carried out at temperatures of between 50 and 200° C.

In the process according to the invention, the yields of benzo-fused heterocycles of formula I are normally between 65% and 80%, including the deacylation step.

The process according to the invention, as described above, is particularly suitable for the preparation of methyl or ethyl 2-aminobenzo[b]thiophene-3-carboxylate. According to the invention, this is done by reacting methyl or ethyl 2-acetylaminotetrahydrobenzothiophene-3-carboxylate with a catalytic amount of a noble metal catalyst in the presence of a hydrogen acceptor and then deacetylating the acetylated amino group by the addition of an amine.

The invention further relates to the use of methyl or ethyl 2-aminobenzo[b]thiophene-3-carboxylate, prepared by the process described above, as an intermediate in the synthesis of 4-[4-(3-chloro-4-methoxybenzylamino)benzo[4,5]thieno [2,3-d]pyrimidin-2-yl]cyclohexanecarboxylic acid, which is known from WO 99/55708. Other intermediates in the synthesis of 4-[4-(3-chloro-4-methoxybenzylamino)benzo [4,5]thieno[2,3-d]pyrimidin-2-yl]cyclohexanecarboxylic acid, starting from methyl 2-aminobenzo[b]thiophene-3-carboxylate, are methyl 4-(4-hydroxybenzo[4,5]thieno[2,3-d]pyrimidin-2-yl)cyclohexanecarboxylate, methyl 4-(4-chlorobenzo[4,5]thieno[2,3-d]pyrimidin-2-yl) cyclohexanecarboxylate and methyl 4-[4-(3-chloro-4-methoxybenzylamino)benzo[4,5]thieno[2,3-d]pyrimidin-2-yl]cyclohexanecarboxylate.

The process known from WO 99/55708 for the preparation of 4-[4-(3-chloro-4-methoxybenzylamino)benzo[4,5] thieno[2,3-d]pyrimidin-2-yl]cyclohexanecarboxylic acid comprises the following steps:

Step a) methyl 2-aminotetrahydrobenzothiophene-3-carboxylate is first cyclized with methyl 4-cyanocyclohexanecarboxylate;

Step b) the tetrahydrobenzothiophene unit of the intermediate formed is dehydrogenated with sulfur to give the compound methyl 4-(4-hydroxybenzo[4,5]thieno[2,3-d] pyrimidin-2-yl)cyclohexanecarboxylate;

Step c) the hydroxyl group is chlorinated by reaction with a chlorinating agent, preferably POCl$_3$;

Step d) the compound methyl 4-(4-chlorobenzo[4,5]thieno [2,3-d]pyrimidin-2-yl)cyclohexanecarboxylate from step c) is reacted with 3-chloro-4-methoxybenzylamine to give the ester methyl 4-[4-(3-chloro-4-methoxybenzylamino) benzo[4,5]thieno[2,3-d]pyrimidin-2-yl] cyclohexanecarboxylate;

Step e) the ester from step d) is saponified; and

Step f) the free acid is converted to a pharmacologically acceptable salt.

For ecological reasons, however, reaction with elemental sulfur is impracticable on the industrial scale.

The invention therefore relates to a process for the preparation of 4-[4-(3-chloro-4-methoxybenzylamino)benzo[4,5] thieno[2,3-d]pyrimidin-2-yl]cyclohexanecarboxylic acid or one of the pharmaceutically acceptable salts, characterized in that it comprises the following steps:

Step a) alkyl 2-acetylaminotetrahydrobenzothiophene-3-carboxylate is reacted according to one or more of claims 1 to 7 with a catalytic amount of a noble metal catalyst in the presence of a hydrogen acceptor, and the acetylated amino group is then deacetylated by the addition of an amine to give the compound alkyl 2-aminobenzo[b] thiophene-3-carboxylate;

Step b) the alkyl 2-aminobenzo[b]thiophene-3-carboxylate is cyclized by reaction with alkyl 4-cyanocyclohexanecarboxylate;

Step c) the hydroxyl group of the compound alkyl 4-(4-hydroxybenzo[4,5]thieno[2,3-d]pyrimidin-2-yl) cyclohexanecarboxylate from step b) is chlorinated with a chlorinating agent;

Step d) the compound alkyl 4-(4-chlorobenzo[4,5]thieno[2, 3-d]pyrimidin-2-yl)cyclohexanecarboxylate from step c) is reacted with 3-chloro-4-methoxybenzylamine to give the ester alkyl 4-[4-(3-chloro-4-methoxybenzylamino) benzo[4,5]thieno[2,3-d]pyrimidin-2-yl] cyclohexanecarboxylate;

Step e) the ester from step d) is saponified; and

Step f) the free acid is converted to a pharmacologically acceptable salt.

The alkyl ester is for example the methyl, ethyl, propyl or butyl ester. It is preferred to use methyl or ethyl 2-acetylaminotetrahydrobenzothiophene-3-carboxylate as the alkyl 2-acetylaminotetrahydrobenzothiophenecarboxylate and all the subsequent intermediates based on this ester unit. It is preferred to use methyl trans-4-cyanocyclohexanecarboxylate as the alkyl 4-cyanocyclohexanecarboxylate and all the subsequent intermediates based on this ester unit.

The reaction conditions of the cyclization b) in the preparation according to the invention of 4-[4-(3-chloro-4-methoxybenzylamino)benzo[4,5]thieno[2,3-d]pyrimidin-2-yl]cyclohexanecarboxylic acid are known from Eur. J. Med. Chem. 1988, 23, 453.

Examples of suitable chlorinating agents are POCl$_3$, SOCl$_2$ or cyanuric chloride. Chlorination with POCl$_3$ or SOCl$_2$ takes place under reaction conditions known to those skilled in the art. The reaction preferably takes place in an inert solvent, for example in toluene, methylene chloride or dimethylformamide.

The reactions of methyl 4-(4-chlorobenzo[4,5]thieno[2,3-d]pyrimidin-2-yl)cyclohexanecarboxylate in steps d) and e) of the process according to the invention for the preparation of 4-[4-(3-chloro-4-methoxybenzylamino)benzo[4,5]thieno [2,3-d]pyrimidin-2-yl]cyclohexanecarboxylic acid, as described above, and step f) are known from WO 99/55708, Example 1, pp. 11–12, and Example 2, p. 14.

The invention further relates to the use of methyl or ethyl 2-aminobenzo[b]thiophene-3-carboxylate, prepared by the process described above, as an intermediate in the synthesis of 4-[4-(3-chloro-4-hydroxybenzylamino)benzo[4,5]thieno [2,3-d]pyrimidin-2-yl]cyclohexanecarboxylic acid, which is known from WO 00/78767. Other intermediates in the synthesis of 4-[4-(3-chloro-4-hydroxybenzylamino)benzo [4,5]thieno[2,3-d]pyrimidin-2-yl]cyclohexanecarboxylic acid, starting from methyl 2-aminobenzo[b]thiophene-3-carboxylate, are methyl 4-(4-hydroxybenzo[4,5]thieno[2,3-d]pyrimidin-2-yl)cyclohexanecarboxylate, methyl 4-(4-chlorobenzo[4,5]thieno[2,3-d]pyrimidin-2-yl) cyclohexanecarboxylate and methyl 4-[4-(3-chloro-4-hydroxybenzylamino)benzo[4,5]thieno[2,3-d]pyrimidin-2-yl]cyclohexanecarboxylate.

In the process known from WO 00/78767 for the preparation of 4-[4-(3-chloro-4-hydroxybenzylamino)benzo[4,5] thieno[2,3-d]pyrimidin-2-yl]cyclohexanecarboxylic acid, methyl 4-(4-chlorobenzothieno[2,3-d]pyrimidin-2-yl) cyclohexanecarboxylate is reacted with 3-chloro-4-hydroxybenzylamine, the methyl 4-(4-chloro-benzothieno [2,3-d]pyrimidin-2-yl)cyclohexanecarboxylate being prepared, as also described in WO 99/55708, by the cyclization of methyl 2-amino-5,6,7,8-tetrahydrobenzothiophene-3-carboxylate with methyl 3-cyanocyclohexanecarboxylate, dehydrogenation with sulfur and subsequent chlorination with phosphorus oxychloride/dimethylamine.

For ecological reasons, however, reaction with elemental sulfur is impracticable on the industrial scale.

The invention therefore relates to a process for the preparation of 4-[4-(3-chloro-4-hydroxybenzylamino)benzo[4,5] thieno[2,3-d]pyrimidin-2-yl]cyclohexanecarboxylic acid or one of the pharmaceutically acceptable salts, characterized in that it comprises the following steps:

Step a) alkyl 2-acetylaminotetrahydrobenzothiophene-3-carboxylate is reacted according to one or more of claims 1 to 7 with a catalytic amount of a noble metal catalyst in the presence of a hydrogen acceptor, and the acetylated amino group is then deacetylated by the addition of an amine to give the compound alkyl 2-aminobenzo[b] thiophene-3-carboxylate;

Step b) the alkyl 2-aminobenzo[b]thiophene-3-carboxylate is cyclized by reaction with alkyl 4-cyanocyclohexanecarboxylate;

Step c) the hydroxyl group of the compound alkyl 4-(4-hydroxybenzo[4,5]thieno[2,3-d]pyrimidin-2-yl) cyclohexanecarboxylate from step b) is chlorinated with a chlorinating agent;

Step d) the compound alkyl 4-(4-chlorobenzo[4,5]thieno[2,3-d]pyrimidin-2-yl)cyclohexanecarboxylate from step c) is reacted with 3-chloro-4-hydroxybenzylamine to give the ester alkyl 4-[4-(3-chloro-4-hydroxybenzylamino) benzo[4,5]thieno[2,3-d]pyrimidin-2-yl]cyclohexanecarboxylate;

Step e) the ester from step d) is saponified; and

Step f) the free acid is converted to a pharmacologically acceptable salt.

The definitions of the term alkyl ester and the reaction conditions of the cyclization and chlorination, as described above for 4-[4-(3-chloro-4-methoxybenzylamino)benzo[4,5]thieno[2,3-d]pyrimidin-2-yl]cyclohexanecarboxylic acid, also apply to the compound 4-[4-(3-chloro-4-hydroxybenzylamino)benzo[4,5]thieno[2,3-d]pyrimidin-2-yl]cyclohexanecarboxylic acid. The reaction conditions of steps d) to f) are known from WO 99/55708, Examples 1 and 2, and from WO 00/78767, Examples 1 and 7.

In the following examples and also in the above explanations, the temperatures are given in °C. In the examples, "conventional work-up" has the following meaning: water is added if necessary, the pH is adjusted to between 2 and 10 if necessary, depending on the constitution of the end product, extraction is carried out with ethyl acetate or dichloromethane and the organic phase is separated off, dried over sodium sulfate, evaporated and purified by chromatography on silica gel and/or by crystallization.

EXAMPLE 1

A suspension of 22.9 g of palladium on activated carbon (5% Pd/C) (Degussa-Hüls; E 101 Rw 5%, 53.9% moisture content) in 260 ml of xylene is refluxed in a water separator until no more water separates off. A solution of 49.7 g of N-acetylthiophenenitrile in 210 ml of xylene is added to this reaction mixture at room temperature and the reaction mixture is heated to 143° C. 48 g of α-methylstyrene are added after 2 h and a further 25 g of α-methylstyrene are added after 96 h. Deacylation is started by the addition of 47 g of pyrrolidine after a reaction time of 127 h, the temperature being kept at 137° C. After a reaction time of 48 h, the mixture is filtered hot and the residue is rinsed with 100 ml of ethyl acetate and 200 ml of 10% HCl solution. The organic phase is washed with distilled water until the pH of the washings is 4. The organic solvent is distilled off to give 2-aminobenzo[b]thiophene-3-carbonitrile in a yield of 81%.

EXAMPLE 2

2 g of palladium catalyst (5% Pd/C, approx. 50% moisture content; Degussa-Hüls; E 101 RW 5%) are added to a solution of 10 g of ethyl 2-acetylaminotetrahydrobenzothiophenecarboxylate in 80 ml of mesitylene and the mixture is heated to 170° under nitrogen. 2 g of ethyl cinnamate are metered in over 30 min and stirring is continued for 21 h. The temperature is then lowered to 100° and 10 ml of pyrrolidine are added. The reaction mixture is stirred for 25 h under nitrogen. The catalyst is then filtered off and rinsed with 60 g of ethanol. The solutions are combined and the solvent is distilled off. The residue is taken up in ethyl acetate and washed twice with 1 N HCl and once with water. After distillation of the solvent and subsequent crystallization from 2-propanol, ethyl 2-aminobenzo[b]thiophene-3-carboxylate is obtained with a yield of 64%.

EXAMPLE 3

14.4 g of hydrogenation catalyst (Degussa-Hüls; E 101 R/W 5%) are added to a solution of 36 g of ethyl 2-acetylaminotetrahydrobenzothiophene-3-carboxylate in 250 ml of xylene (isomeric mixture) and the mixture is heated to a constant temperature of 139° C. to 141° C. 47 g of α-methylstyrene are metered in over a period of 5 h. The mixture is then refluxed for a further 36 h. It is cooled to 102° C., 32 g of pyrrolidine are added and the mixture is brought back to the reflux point (127° C.); it is stirred for 20 h at this temperature. After cooling to 20° C., the Pd/carbon is filtered off, the filtrate is concentrated to a residue, and the residue is taken up in 75 ml of ethyl acetate and washed with three times 12 ml of 10% hydrochloric acid. The organic phase is washed with twice 5 ml of water and then concentrated to a residue. This is recrystallized from 50 ml of isopropanol to give 21 g of ethyl 2-aminobenzothiophene-3-carboxylate in the form of slightly yellowish crystals (70.5% yield).

The other synthetic steps are known from Eur. J. Med. Chem. 1988, 23, 453 and WO 99/55708, Example 1, pp. 11–12, and Example 2, p. 14.

What is claimed is:

1. Process for the preparation of benzo-fused heterocycles of general formula I:

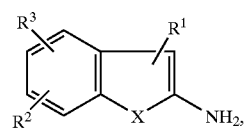

in which

X is S, O or NH,

R$^1$ is CN, NO$_2$, Ac, COAr, COOAr, COOH, COOA or CONR$^4$R$^5$,

R$^2$ and R$^3$ independently of one another are each H, A, NO$_2$, CN, OH, OA or Ac, R$^4$ and R$^5$ independently of one another are each H, A, Ar or Ac, or R$^4$ and R$^5$ together are —(CH$_2$)—(CH$_2$)$_n$—(CH$_2$)—, A is alkyl having 1–6 C atoms, Ac is acyl having 1–6 C atoms, Ar is unsubstituted phenyl or phenyl substituted by A, NO$_2$, CN, OH or OA, and n is 2, 3 or 4, by reacting tetrahydrobenzo-fused heterocycles of formula II:

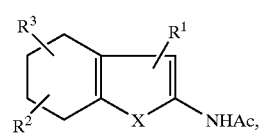

in which

X is S, O or NH,

R$^1$ is CN, NO$_2$, Ac, COAr, COOAr, COOH, COOA or CONR$^4$R$^5$,

R² and R³ independently of one another are each H, A, NO₂, CN, OH, OA or Ac,

R⁴ and R⁵ independently of one another are each H, A, Ar or Ac, or

R⁴ and R⁵ together are —(CH₂)—(CH₂)—(CH₂)—,

A is alkyl having 1–6 C atoms,

Ac is acyl having 1–6 C atoms,

Ar is unsubstituted phenyl or phenyl substituted by A, NO₂, CN, OH or OA, and n is 2, 3 or 4, with a catalytic amount of a noble metal catalyst in the presence of a hydrogen acceptor and then deacylating the acylated amino group by the addition of an amine.

2. Process according to claim 1 for the preparation of methyl or ethyl 2-aminobenzo[b]thiophene-3-carboxylate.

3. Process according to claim 1, wherein the noble metal catalyst comprises palladium on activated carbon, carbon, aluminium oxide, barium carbonate, barium sulfate, calcium carbonate or strontium carbonate, platinum on activated carbon, carbon or aluminium oxide, or rhodium on carbon or aluminium oxide.

4. Process according to claim 1, wherein the hydrogen acceptor comprises styrene, α-methylstyrene, stilbene, a tolans, a cinnamic acid esters, cyclohexene, oxygen or an oxygen/gas mixture.

5. Process according to claim 1, wherein the amine comprises a primary or secondary amine boiling at 50–200° C.

6. Process according to claim 1, wherein the reactions are carried out at a temperature of 50–200° C.

7. Process according to claim 1, wherein the reactions are carried out in a high-boiling solvent.

8. A process for synthesizing 4-[4-(3-chloro-4-methoxybenzylamino)benzo[4,5]thieno[2,3-d]pyrimidin-2-yl]cyclohexanecarboxylic acid, comprising reacting an intermediate comprising methyl or ethyl 2-aminobenzo[b]thiophene-3-carboxylate with methyl 4-cyanocyclohexanecarboxylate.

9. Process for the preparation of 4-[4-(3-chloro-4-methoxybenzylamino)benzo [4,5]thieno [2,3-d]-pyrimidin-2-yl]cyclohexanecarboxylic acid or one of the pharmaceutically acceptable salts, comprising:

a) reacting alkyl 2-acetylaminotetrahydrobenzothiophene-3-carboxylate according to claim 1 with a catalytic amount of a noble metal catalyst in the presence of a hydrogen acceptor, and then deacetylating the acetylated amino group by the addition of an amine to give the compound an alkyl 2-aminobenzo-[b]thiophene-3-carboxylate;

b) cyclizing the alkyl 2-aminobenzo[b]thiophene-3-carboxylate by reaction with alkyl 4-cyanocyclohexanecarboxylate;

c) chlorinating the hydroxyl group of the compound alkyl 4-(4-hydroxybezo[4,5]thieno[2,3-d]pyrimidin-2-yl)cyclohexanecarboxylate from b) with a chlorinating agent;

d) reacting the compound alkyl 4-(4-chlorobenzo[4,5]thieno[2,3-d]pyrimidin-2-yl)cyclohexanecarboxylate from c) with 3-chloro-4-methoxybenzylamine to give the ester alkyl 4-[4-(3-chloro-4-methoxybenzylamino)benzo[4,5]thieno[2,3-d]pyrimidin-2-yl]cyclohexanecarboxylate;

e) saponifying the ester from d); and f) converting the free acid to a pharmacologically acceptable salt.

10. A process for synthesizing 4-4-(3-chloro-4-hydroxybenzylamino)benzo[4,5]thieno[2,3-d]pyrimidin-2-yl]cyclohexanecarboxylic acid, comprising reacting an intermediate comprising methyl or ethyl 2-aminobenzo[b]thiophene-3-carboxylate with methyl 3-cyano-cyclohexanecarboxylate.

11. Process for the preparation of 4-[4-(3-chloro-4-hydroxybenzylamino)benzo [4,5]thieno [2,3-d]-pyrimidin-2-yl]cyclohexanecarboxylic acid or one of the pharmaceutically acceptable salts, comprising:

a) reacting alkyl 2-acetylaminotetrahydrobenzothiophene-3-carboxylate according to claim 1 with a catalytic amount of a noble metal catalyst in the presence of a hydrogen acceptor, and then deacetylating the acetylated amino group by the addition of an amine to give the compound alkyl 2-aminobenzo-[b]thiophene-3-carboxylate;

b) cyclizing the alkyl 2-aminobenzo[b]thiophene-3-carboxylate by reaction with alkyl 4-cyanocyclohexanecarboxylate;

c) chlorinating the hydroxyl group of the compound alkyl 4-(4-hydroxybezo[4,5]thieno[2,3-d]pyrimidin-2-yl)cyclohexanecarboxylate from b) with a chlorinating agent;

d) reacting the compound alkyl 4-(4-chlorobenzo[4,5]-thieno[2,3-d]pyrimidin-2-yl)cyclohexanecarboxylate from c) with 3-chloro-4-hydroxybenzylamine to give the ester alkyl 4-[4-(3-chloro-4-hydroxybenzylamino)benzo-[4,5]thieno[2,3-d]pyrimidin-2-yl]cyclohexanecarboxylate;

e) saponifying the ester from d); and f) converting the free acid to a pharmacologically acceptable salt.

12. A process according to claim 1, wherein A is methyl or ethyl.

13. A process according to claim 1, wherein Ac is acetyl.

14. A process according to claim 1, wherein Ar is unsubstituted phenyl.

15. A process according to claim 1, wherein R¹ is COOA.

16. A process according to claim 1, wherein R²–R⁵ are H.

* * * * *